(12) United States Patent
Hiki

(10) Patent No.: US 7,534,218 B2
(45) Date of Patent: May 19, 2009

(54) WALKING ASSISTING DEVICE

(75) Inventor: Yutaka Hiki, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 128 days.

(21) Appl. No.: 11/774,294

(22) Filed: Jul. 6, 2007

(65) Prior Publication Data

US 2008/0009778 A1 Jan. 10, 2008

(30) Foreign Application Priority Data

Jul. 10, 2006 (JP) ............................. 2006-189188

(51) Int. Cl.
*A61F 5/00* (2006.01)
(52) U.S. Cl. .......................................... 602/16; 602/23
(58) Field of Classification Search ...................... 602/5, 602/16, 19, 23–24, 26–27; 482/51
See application file for complete search history.

(56) References Cited

U.S. PATENT DOCUMENTS 4,543,948 A * 10/1985 Phillips et al. ................. 602/23
4,964,628 A * 10/1990 Poplawski ..................... 482/51
5,961,476 A * 10/1999 Betto et al. .................... 602/16
2006/0276728 A1* 12/2006 Ashihara et al. ................ 601/5

FOREIGN PATENT DOCUMENTS

JP 2003-220102 8/2003

* cited by examiner

*Primary Examiner*—Michael A. Brown
(74) *Attorney, Agent, or Firm*—Rankin, Hill & Clark LLP (57) ABSTRACT

A walking assisting device that transmits a force generated by a leg link to a user's trunk via a load transfer portion. The leg link includes a first link connected to the load transfer portion via a first joint portion, a second link connected to a foot attachment portion via a second joint portion, a third joint portion which connects the first link to the second link so as to be free to bend and stretch, and a driving source which drives the third joint portion. Even if a flexion angle of the third joint portion reaches zero degree, the controllability is maintained in the direction of pushing up the load transfer portion so that the leg link can be extended straight with the user's leg extended straight. An interlock system retracts and extends the second link and increases and decreases the flexion angle of the third joint portion.

6 Claims, 6 Drawing Sheets

WALKING ASSISTING DEVICE

BACKGROUND OF THE INVENTION

1. Field of the Invention

The present invention relates to a walking assisting device for assisting a user in walking.

2. Description of the Related Art

Conventionally, as with this type of walking assisting device, there is known a trunk attachment portion attached to the user's trunk, a thigh attachment portion attached to a thigh of a user's leg with being connected to the trunk attachment portion via a hip joint portion corresponding to a human hip joint, a crus attachment portion attached to the crus of the user's leg with being connected to the thigh attachment portion via a knee joint portion corresponding to a human knee joint, and a foot attachment portion attached to a user's foot with being connected to the crus attachment portion via an ankle joint portion corresponding to a human ankle joint. Driving sources which drive the joint portions are provided coaxially with the joint portions, respectively (refer to Japanese Patent Laid-Open No. 2003-220102, for example). This type of walking assisting device is capable of assisting the user in walking by applying an assist moment from a driving source for the hip joint portion to the user's thigh via the thigh attachment portion, applying an assist moment from a driving source for the knee joint portion to the users crus via the crus attachment portion, and applying an assist moment from a driving source for the ankle joint portion to the user's foot via the foot attachment portion.

The above conventional walking assisting device is capable of assisting all movements of the user's thigh, crus, and foot, the thigh and the crus are restrained by the thigh attachment portion and the crus attachment portion. However, the user has an extremely constrained feeling. In addition, it is necessary to provide the driving sources for the joint portions such as the hip joint portion, the knee joint portion, and the ankle joint portion, which increases the cost disadvantageously.

In order to solve the above problem, it is conceivable to adapt the walking assisting device to include a load transfer portion, a foot attachment portion attached to the user's foot, and a leg link between the load transfer portion and the foot attachment portion wherein a force generated by the leg link is transmitted to the user's trunk via the load transfer portion. According thereto, the walking assisting device can assist walking by reducing the load on the user's leg by means of the force from the leg link transmitted to the user's trunk via the load transfer portion. Furthermore, it is possible to reduce the constrained feeling by making the leg link freed from the user's leg. In this condition, if the leg link includes an upper first link which is connected to the load transfer portion via a first joint portion, a lower second link which is connected to the foot attachment portion via a second joint portion, a middle third joint portion which connects the first link to the second link in such a way that they can bend and stretch freely, and a driving source which drives the third joint portion, the load on the user's leg can be reduced. This is accomplished by generating a force in the direction of decreasing a flexion angle of the third joint portion (in the direction of extending the leg link) by means of the driving source.

In the above, the leg link is freed from the user's leg and a force of bending the knee joint is not applied to the user's leg even if the leg link is bent in a condition where the user stands upright with his leg extending straight. This, however, causes the third joint portion of the leg link to project forward of the user's knee joint when the user stands upright and it brings discomfort to the user. Therefore, it is desirable that the flexion angle of the third joint portion is zero degree. In other words, the leg link is extended with the user's leg extending straight. This, however, causes a problem described below.

Specifically, in the case of the leg link which bends and stretches at the third joint portion, the extension speed of the leg link becomes zero when the flexion angle of the third joint portion reaches zero degree, where the extension speed is obtained by differentiating the length of the leg link (the length of a line segment between the first joint portion at the upper end of the leg link and the second joint portion at the lower end of the leg link) with respect to the flexion angle of the third joint portion. The result is a loss of controllability in the direction of extending the leg link, in other words, in the direction of pushing up the load transfer portion. Therefore, if the walking assisting device is adapted to have a zero degree of flexion angle of the third joint portion with the user's leg extending straight, it cannot appropriately control the upward force of the load transfer portion generated by the leg link so as to cope with a change in load even in a situation where the load changes because the user stands on one leg with the leg extending straight or the like. It is therefore necessary to prevent the loss of the controllability in the direction of pushing up the load transfer portion by bringing the leg link to be bent more or less with the user's leg extending straight, which results in bringing discomfort to the user.

In view of the above problem, an object of the present invention is to provide a walking assisting device that can be used by a user without feeling uncomfortable by enabling a leg link to be extended with a user's leg extending straight while maintaining the controllability in the direction of pushing up the load transfer portion also when the leg link is extended.

SUMMARY OF THE INVENTION

To achieve the above object, according to an aspect of the present invention, there is provided a walking assisting device having a load transfer portion, a foot attachment portion attached to a user's foot, and a leg link between the load transfer portion and the foot attachment portion, in which a force generated by the leg link is transmitted to a user's trunk via the load transfer portion. The leg link includes an upper first link connected to the load transfer portion via a first joint portion, a lower second link connected to a foot attachment portion via a second joint portion, a middle third joint portion which connects the first link to the second link so as to be free to bend and stretch, and a driving source which drives the third joint portion. At least one of the first link and the second link is formed by an extensible and retractable link, which can be freely extended and retracted, and an interlock system is provided which retracts and extends the extensible and retractable link in conjunction with the operation of increasing and decreasing a flexion angle of the third joint portion.

According to the present invention, the extensible and retractable link constituting at least one of the first link and the second link extends along with a decrease in the flexion angle of the third joint portion. Therefore, it is possible to prevent the extension speed of the extensible and retractable link (the speed obtained by differentiating the length of the extensible and retractable link with respect to the flexion angle of the third joint portion) from being zero even if the flexion angel of the third joint portion reaches zero degree. According thereto, the extension speed of the leg link does not become zero where the extension speed is obtained by differentiating the length of the leg link (the length of a line segment between the first joint portion at the upper end of the leg link and the second joint portion at the lower end) with respect to the flexion angle of the third joint portion. Therefore, even if the flexion angle of the third joint portion reaches zero degree, the walking assisting device doest not lose the controllability in the direction of pushing up the load transfer portion and can appropriately control an upward force of the load transfer portion applied by the leg link in response to a load change. Consequently, it becomes possible to bring the flexion angle of the third joint portion to zero degree. In other words, it becomes possible to extend the leg link with the user's leg extending straight, whereby the user can use the walking assisting device without feeling uncomfortable.

Furthermore, it is possible to form the interlock system by providing a driving source for use in extending and retracting the extensible and retractable link and a sensor for detecting the flexion angle of the third joint portion so that the driving source for extension and retraction is operated to extend and retract the extensible and retractable link based on a signal from the sensor. This, however, increases the cost and the total weight of the leg link due to the effect of the driving source for extension and retraction. On the other hand, if the interlock system is formed by a mechanical system which converts a rotary motion of the third joint portion or a rotary motion of the driving source for the third joint portion to a linear motion for extending and retracting the extensible and retractable link, the cost is reduced and the increase in the total weight of the leg link can be held down advantageously.

DETAILED DESCRIPTION OF THE PREFERRED EMBODIMENTS

Figure 1:
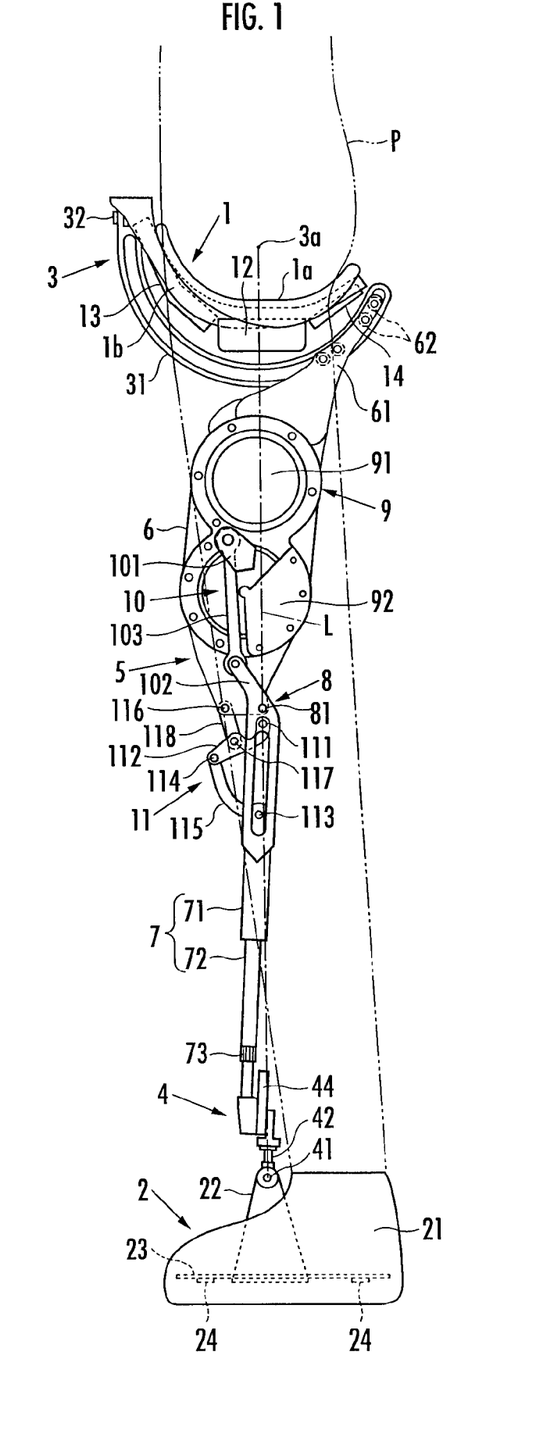
FIG. 1 is a side view of a walking assisting device according to a first embodiment of the present invention.
Figure 2:
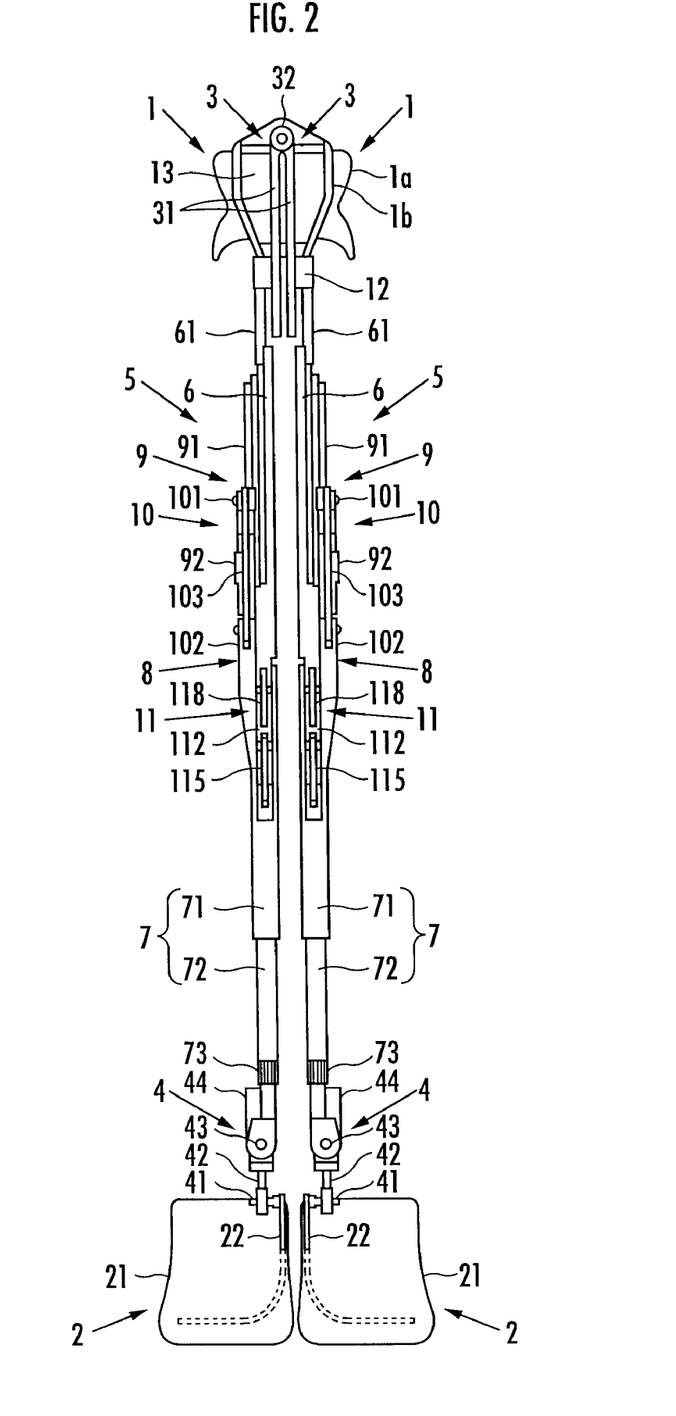
FIG. 2 is a front view of the walking assisting device according to the first embodiment.

A walking assisting device according to embodiments of the present invention will now be described hereinafter. As shown in FIG. 1 and FIG. 2, the walking assisting device includes a seat member 1 which is a load transfer portion which a user P sits astride, a pair of left and right foot attachment portions 2, 2 which are attached to user's left and right feet, and a pair of left and right leg links 5, 5 which are connected to the seat member 1 each via a first joint portion 3 located at the upper end and connected to the two foot attachment portions 2, 2 each via a second joint portion 4 located at the lower end.

Each leg link 5 is composed of a freely bending and stretching link which varies a distance between the first joint portion 3 and the second joint portion 4. More specifically, each leg link 5 includes an upper first link 6 connected to the seat member 1 via the first joint portion 3 and a lower second link 7 connected to each foot attachment portion 2 via a second joint portion 4, which are connected by a middle third joint portion 8 in such a way that the leg link 5 is free to bend and stretch. Each leg link 5 is equipped with a driving source 9 for the third joint 8. A force in the direction of extension is applied to each leg link 5 by driving the third joint portion 8 by means of the driving source 9 to generate a supporting force which supports at least a part of the user's weight (hereinafter, referred to as a weight relief assist force). The weight relief assist force generated in each leg link 5 is transmitted to the trunk of the user P via the seat member 1 and the load on the leg of the user P is thereby reduced.

The user P can use the walking assisting device according to this embodiment only by wearing the foot attachment portions 2 on his feet and sitting on the seat member 1, without having a constrained feeling almost at all. Moreover, the first joint portions 3 and the leg links 5 are located under the crotch of the user P and therefore the user P does not hit his hands against the first joint portions 3 and the Leg links 5 when swinging his arms in walking, by which he can swing his arms freely. Furthermore, the walking assisting device is compact in size and it can be used in a small place, by which the usability is remarkably improved in addition to the reduction in constrained feeling and the secured free arm swing.

The seat member 1 is composed of a saddle-shaped seat portion 1a which the user P sits on and a support frame 1b on the underside thereof which supports the seat portion 1a. In addition, each first joint portion 3 for each leg link 5 has an arc-shaped guide rail 31 which is longitudinal in the anteroposterior direction provided on the downside of the seat member 1. Then, each leg link 5 is movably engaged with the guide rail 31 via a plurality of rollers 62 pivotally attached to a slider 61 which is fixed to the upper end of the first link 6. In this way, each leg link 5 swings in the forward/backward direction around the center of curvature of the guide rail 31 and the forward/backward swing fulcrum of each leg link 5 functions as the center of curvature of the guide rail 31.

Referring to FIG. 1, the center of curvature of the guide rail 31, namely the forward/backward swing fulcrum 3a of each leg link 5 in each first joint portion 3 is located above the seat member 1. If the user P bends his upper body forward or the like in this condition and thereby the action point of the weight of the upper body of the user P relative to the seat member 1 is misaligned forward of the forward/backward swing fulcrum 3a of each leg link 5, the seat member 1 inclines forward and downward. If the seat member 1 continues to incline further, it is misaligned backward relative to the user P. In this embodiment, however, the action point of the weight is displaced backward under the swing fulcrum 3a along with the forward and downward inclination of the seat member 1 and thereby the anteroposterior distance between the fulcrum 3a and the action point of the weight decreases, which thereby decreases the angular moment applied to the seat member 1. Thereafter, the angular moment applied to the seat member 1 becomes zero when the action point of the weight is displaced to the position just under the swing fulcrum 3a, which stabilizes the seat member 1 in this state. Since the seat member 1 automatically converges on the stable state as described above, it is possible to prevent the seat member 1 from being misaligned in the forward/backward direction under the crotch of the user P.

Furthermore, the slider 61, which is located at the upper end of each leg link 5, engages with a part of the guide rail 31, which is located backward of a line between the third joint portion 8 of the leg link 5 and the forward/backward swing fulcrum 3a (the center of curvature of the guide rail 31) of the leg link 5. This secures a forward swing stroke of each leg link 5 that follows the forward swing motion of each leg of the user P without a need for increasing the length of the guide rail 31 so much.

Furthermore, the guide rails 31 for the left and right leg links 5 are pivotally supported by the support frame 1b of the seat member 1 via an anteroposterior spindle 32. Therefore, the guide rails 31 are connected to the seat member 1 so as to be free to swing in the lateral direction. Therefore, the leg links 5 are allowed to swing in the lateral direction, which enables the user P to abduct his legs.

Each foot attachment portion 2 has a shoe 21 and a joint member 22 which protrudes upward from the inside of the shoe 21. Moreover, the second link 7 of each leg link 5 is connected to the joint member 22 via the second joint portion 4. The second joint portion 4 is formed to a three-axis structure including a first shaft 41 extending in the lateral direction, a second shaft 42 extending in the vertical direction, and a third shaft 43 extending in the anteroposterior direction. In addition, a two-axis force sensor 44 is incorporated into the second joint portion 4. Note here that the above weight relief assist force is applied onto a line (hereinafter, referred to as reference line) L between the forward/backward swing fulcrum 3a of the leg link 5 in the first joint portion 3 and the first shaft 41 which the forward/backward swinging fulcrum of the leg link 5 in the second joint portion 4. Then, an actual weight relief assist force applied onto the reference line L (accurately, a resultant force between the weight relief assist force and a force generated by the weights of the seat member 1 and the leg links 5) is calculated based on detected values of forces in the two-axis direction detected by the force sensors 44.

Furthermore, as shown in FIG. 1, a pair of front and back pressure sensors 24, 24 which detect loads on the metacarpophalangeal joint (MP joint) and the heel of each foot of the user P on the undersurface of an insole 23 provided in the shoe 21. In assisting walking, first, a ratio of the applied load on each foot to the total load applied to both feet of the user is calculated based on the detected values of the pressure sensors 24, 24 of each foot attachment portion 2. Subsequently, a control target value of the weight relief assist force which should be generated by each leg link 5 is calculated by multiplying a preset value of the weight relief assist force by a load ratio of each foot. Then, the driving source 9 is controlled so that the actual weight relief assist force calculated based on the detected values of the above force sensor 44 reaches the control target value.

In this regard, the driving source 9 is disposed in the leg link 5, and on the other hand, the driving source 9 is a heavy load. Therefore, an increase in distance between the driving source 9 and the forward/backward swing fulcrum 3a of the leg link 5 in the first joint portion 3 also increases a distance between the centroid of the entire leg link 5 including the driving source 9 and the swing fulcrum 3a. In consequence, the moment of inertia of the leg link 5 grows around the swing fulcrum 3a, and therefore when the user P swings a free leg (a leg with the foot off the floor) forward, a load on the free leg grows due to the moment of inertia of the leg link 5. Therefore, in this embodiment, the driving source 9 is disposed in the portion upper than the third joint portion 8 of the first link 6 so that the centroid of the entire leg link 5 including the driving source 9 is located upper than the third joint portion 8. This decreases the distance between the centroid of the entire leg link 5 and the swing fulcrum 3a and reduces the moment of inertia of the leg link 5 around the swing fulcrum 3a, whereby the load on the free leg of the user P is reduced.

In addition, "the centroid of the entire leg link 5 located upper than the third joint portion 8" means that the mass of the first link 6 is larger than that of the second link 7. Note here that the thigh of a human leg is heavier than the crus thereof. With the arrangement of the centroid of the entire leg link 5 located upper than the third joint portion 8, the mass ratio between the first link 6 and the second link 7 of the leg link 5 gets closer to the mass ratio between the thigh and the crus of the human leg. In addition, the length ratio between the first link 6 and the second link 7 is substantially equal to the length ratio between the thigh and the crus of the human leg. Therefore, the total natural frequency of the user's free leg and the leg link 5, which moves while following the free leg, has a value close to the natural frequency of the free leg only and therefore the user can move the free leg without feeling uncomfortable.

In this embodiment, the driving source 9 includes an electric motor 91 and a planetary gear type reduction gear 92. In this instance, it is conceivable that the electric motor 91 and the reduction gear 92 are disposed coaxially with each other with being located in the vicinity of the upper end of the first link 6. The lateral thickness of the leg link 5, however, is limited to prevent interference with the leg of the user P. Then, if the electric motor 91 and the reduction gear 92 are disposed coaxially with each other, the thickness of the disposed portion of the driving source 9 exceeds the thickness limit of the leg link 5 and the driving source 9 may hit the leg of the user P. Therefore, in this embodiment, the electric motor 91 and the reduction gear 92 are disposed in such a way that the electric motor 91 is located upper than the reduction gear 92 in the first link 6. According thereto, the electric motor 91 that is heavier than the reduction gear 92 is closer to the swing fulcrum 3a than the reduction gear 92. Therefore, the moment of inertia of the leg link 5 around the swing fulcrum 3a can be effectively reduced.

Figure 3:
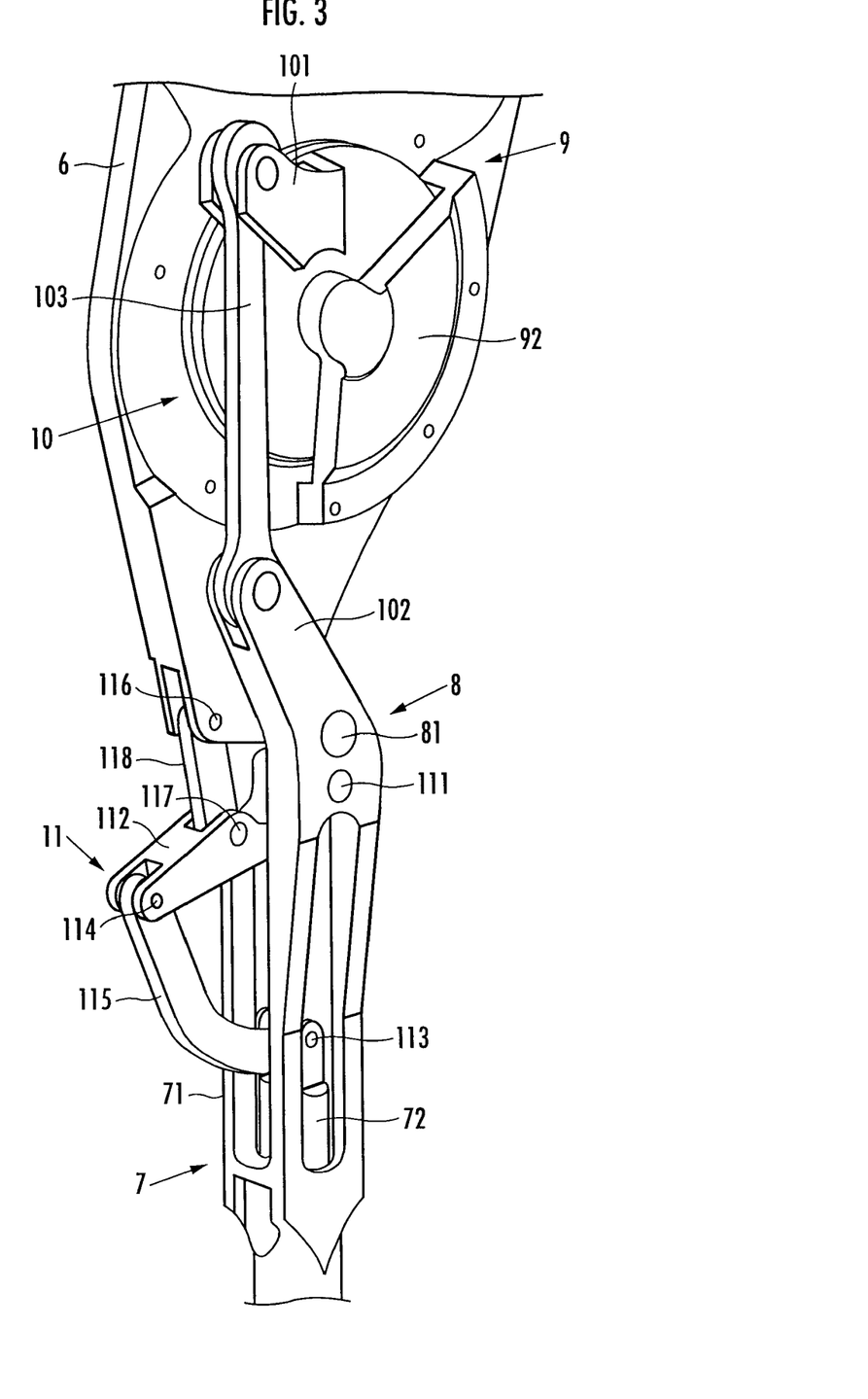
FIG. 3 is a perspective view of components in the vicinity of a third joint portion of a leg link of the walking assisting device according to the first embodiment.
Figure 4:
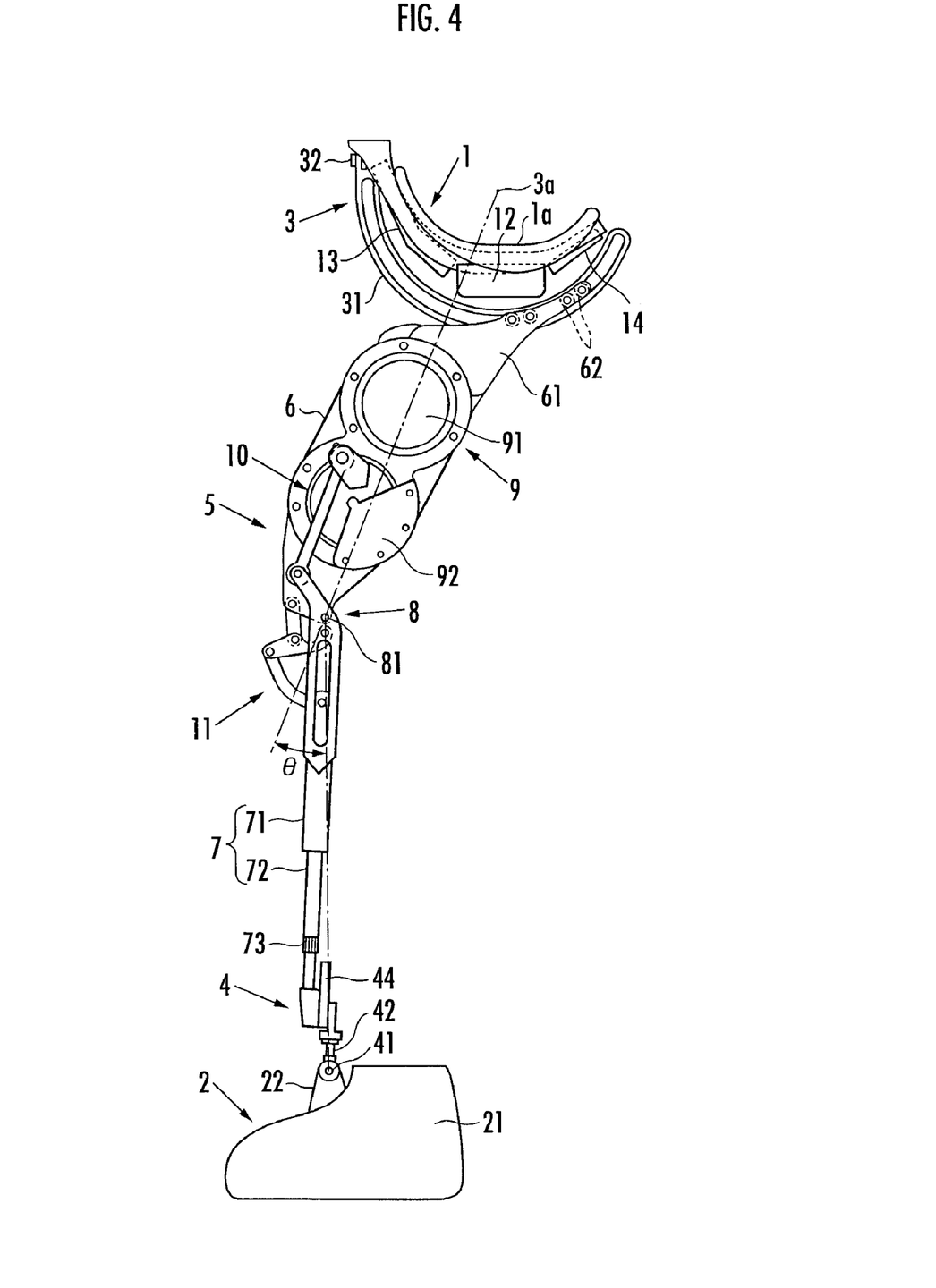
FIG. 4 is a side view of the leg link of the walking assisting device according to the first embodiment when it is bent.

The third joint portion 8 is driven by the electric motor 91 via the reduction gear 92 and a power transmission system 10. It will be described in detail below with reference to FIG. 3. The third joint portion 8 is formed with the upper end of the second link 7 pivotally attached to the lower end of the first link 6 via the lateral joint shaft 81. Furthermore, the power transmission system 10 includes a first crank arm 101 provided on the output side of the reduction gear 92, a second crank arm 102 extending upward from the joint shaft 81 with being integrated with the second link 7, and a rod 103 which connects the crank arms 101 and 102 to each other. According thereto, the rotary output of the reduction gear 92 is transmitted to the second crank arm 102 via the first crank arm 101 and the rod 103, the second link 7 swings around the joint shaft 81 with respect to the first link 6, and the leg link 5 is bent as shown in FIG. 4 from the extended condition shown in FIG. 1.

In the meantime, if the leg link 5 is bent with the leg of the user P extending straight, the third joint portion 8 protrudes forward of the knee joint of the user P and it gives an uncomfortable feeling to the user P. Therefore, in the condition where the leg of the user P extends straight, it is desirable that the joint shaft 81 of the third joint portion 8 is located on the reference line L and that the flexion angle θ of the third joint portion 8 reaches zero degree, in other words, the leg link 5 is extended as shown in FIG. 1.

In this regard, if the leg link 5 is a simple bending and stretching link, the length of a line segment between the swing fulcrum 3a of the leg link 5 in the first joint portion 3 and the first shaft 41 of the second joint portion 4 (hereinafter, referred to as leg link length) varies as indicated by a line B in FIG. 5(a) according to the flexion angle θ of the third joint portion 8. The extension speed of the leg link 5, which is obtained by differentiating the leg link length with respect to the flexion angle θ of the third joint portion 8, varies as indicated by a line B in FIG. 5(b). When the flexion angle θ reaches zero degree, the extension speed of the leg link 5 becomes zero. Therefore, when the flexion angle θ reaches zero degree, the walking assisting device loses the controllability in the direction of extending the leg link 5, in other words, in the direction of pushing up the seat member 1. Accordingly, even if there is an increase in the weight relief assist force which should be generated in the leg link 5 on the standing leg side due to a shift from the state where the user P stands upright on two legs to the state where the user P stands on one leg, it is impossible to appropriately control the weight relief assist force if the standing leg extends straight and the third joint portion 8 of the leg link 5 on the standing leg side has a zero degree of the flexion angle θ.

Therefore, in this embodiment, the second link 7 of the leg link 5 is formed by an extensible and retractable link, which can be freely extended and retracted, including a cylindrical upper half portion 71 connected to the third joint portion 8 and a lower half portion 72 slidably inserted into the upper half portion 71 and supported thereby, and it is further provided with an interlock system 11 which extends and retracts the second link 7 in conjunction with the operation of increasing and decreasing the flexion angle θ of the third joint portion 8. Then, the interlock system 11 is adapted so that the extension speed of the second link 7 does not become zero even if the flexion angle θ is brought to zero degree where the extension speed is obtained by differentiating the length of the second link 7 with respect to the flexion angle θ of the third joint portion 8.

Figure 5:
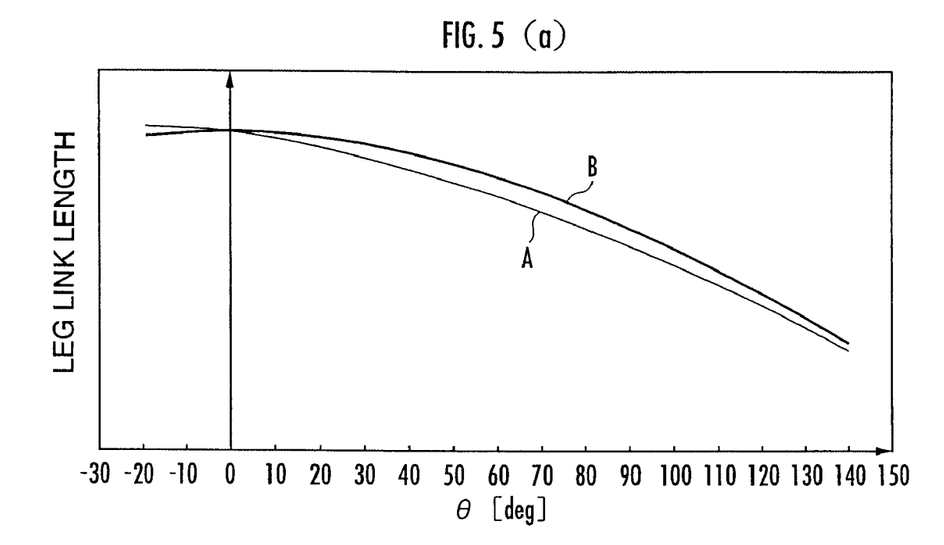
FIG. 5(a) is a graph showing a change in leg link length relative to a flexion angle of the third joint portion.
FIG. 5(b) is a graph showing a change in extension speed of the leg link relative to the flexion angle of the third joint portion.

According thereto, the leg link length varies as indicated by a line A in FIG. 5(a) according to the flexion angle θ. Then, the extension speed of the leg link 5 obtained by differentiating the leg link length with respect to the flexion angle θ varies as indicated by a line A in FIG. 5(b) and does not become zero when the flexion angle θ is zero degree. Therefore, even if the flexion angle θ reaches zero degree, the controllability in the direction of pushing up the seat member 1 is not lost and the weight relief assist force can be appropriately controlled in response to a change in load. Consequently, it becomes possible to cause the flexion angle of the third joint portion 8 to be zero degree with the leg of the user P extending straight, in other words, to cause the leg link 5 to be extended, and therefore the user P can use the walking assisting device without feeling uncomfortable. The lower half portion 72 is adjustable to an arbitrary length by using a lock nut 73. Therefore, the leg link length can be adjusted to the length of the leg of the user P.

In this regard, it is also possible to provide a driving source for extension and retraction of the second link 7 which moves the lower half portion 72 of the second link 7 up and down with respect to the upper half portion 71 and a sensor which detects the flexion angle θ of the third joint portion 8 in order to form an interlock system 11 SO that the lower half portion 72 of the second link 7 is moved up and down by actuating the driving source for extension and retraction according to a signal from the sensor. This, however, increases the cost and the total weight of the leg link 5 due to the effect of the driving source for extension and retraction. Therefore, in this embodiment, the interlock system 11 is formed by a mechanical system which converts the rotary motion of the third joint portion 8 to a linear motion for extending and retracting the second link 7. In other words, the mechanical system converts the rotary motion of the third joint portion 8 to a linear motion of the lower half portion 72 of the second link 7 so as to reduce the cost and to hold down an increase in the total weight of the leg link 5.

More specifically, the interlock system 11 includes a first interlocking link 112 with one end pivotally mounted on the upper half portion 71 of the second link 7 by a shaft 111, a second interlocking link 115 with one end pivotally mounted on the lower half portion 72 of the second link 7 by a shaft 113 and the other end pivotally mounted on the other end of the first interlocking link 112 by a shaft 114, and a third interlocking link 118 with one end pivotally mounted on the first link 6 by a shaft 116 and the other end pivotally mounted on the middle portion of the first interlocking link 112 by a shaft 117. According thereto, a rectangle shape, which is formed by the joint shaft 81, the shaft 111, the shaft 117, and the shaft 116 of the third joint portion 8, deforms by a displacement of the shaft 111 caused by the rotary motion around the third joint portion 8 of the upper half portion 71 of the second link 7 with respect to the first link 6 and this deformation causes a change in an angle between a line segment connecting the shaft 114 to the shaft 111 and a line segment connecting the shaft 114 to the shaft 113. This change in the angle causes a change in distance between the shaft 111 and the shaft 113 and thereby the lower half portion 72 of the second link 7 linearly moves in a longitudinal direction (vertical direction) of the upper half portion 71 with respect thereto. If the flexion angle θ of the third joint portion 8 decreases, the lower half portion 72 moves downward as shown in FIG. 1 and the length of the second link 7 increases. If the flexion angle θ increases, the lower half portion 72 moves upward as shown in FIG. 4 and the length of the second link 7 decreases. Note that the interlock system 11 is not limited to the link mechanism of this embodiment, but it can be formed by a cam mechanism or a rack and pinion mechanism.

Where the first joint portion 3 is formed into an arc-shaped guide rail 31 as described above, a space is generated between the guide rail 31 and the seat member 1 on the underside thereof. Therefore, in order to use the space effectively, a battery 12 for the driving source 9, a controller 13, and a motor driver 14 are disposed in the support frame 1b of the seat member 1 in such a way as to fit into the space between the seat member 1 and the guide rail 31.

In this regard, it is desired that the driving source 9, which is a heavy load, is disposed in a position higher than the third joint portion 8. This reduces the moment of inertia around the swing fulcrum 3a in the first joint portion 3 of the leg link 5. Therefore, in this embodiment, the driving source 9 is disposed in a position upper than the third joint portion 8 of the first link 6 as described above. Furthermore, the battery 12, which is a heavy load, is also disposed in the seat member 1 located higher than the third joint portion 8. If the driving source 9 and the battery 12 are located in higher positions in this manner, the weight of the driving source 9 and that of the battery 12 easily generate a forward/backward tilting moment around the first shaft 41 of the second joint portion 4 in the leg link 5 in the state where the user P stands upright, and the tilting moment causes a forward/backward pushing force to be applied to the seat member 1.

Therefore, in this embodiment, the tilting moment can be prevented from occurring. In this connection, the condition of the leg link 5 in which the user P stands upright is defined as a normal condition (the condition shown in FIG. 1) for description. In the normal condition of the leg link 5, the driving source 9 and the battery 12, which are heavy loads, are disposed in such a way that a plane, which is vertical and parallel to the lateral direction and passes through the first shaft 41 of the second joint portion 4. In other words, a frontal plane (in this embodiment, the frontal plane substantially matches the above reference line L) passes through the anteroposterior width of the driving source 9 and the anteroposterior width of the battery 12. This reduces an anteroposterior offset distance of the centroid of the driving source 9 and the centroid of the battery 12 with respect to the above frontal plane. Therefore, in the normal condition of the leg link 5, the arrangement reduces the anteroposterior tilting moment around the first shaft 41 of the second joint portion 4 generated in the leg link 5 by the weight of the driving source 9 and that of the battery 12. Consequently, the anteroposterior pushing force applied to the seat member 1 due to the tilting moment is also reduced in the state where the user P stands upright, thereby improving the stability.

It is also possible to dispose the battery 12 in the first link 6 of the leg link 5. If, however, the battery 12 is disposed in the seat member 1 as described in this embodiment, the mass of the battery 12 is not added to the leg link 5 and therefore the moment of inertia of the leg link 5 can be reduced as possible advantageously.

Figure 6:
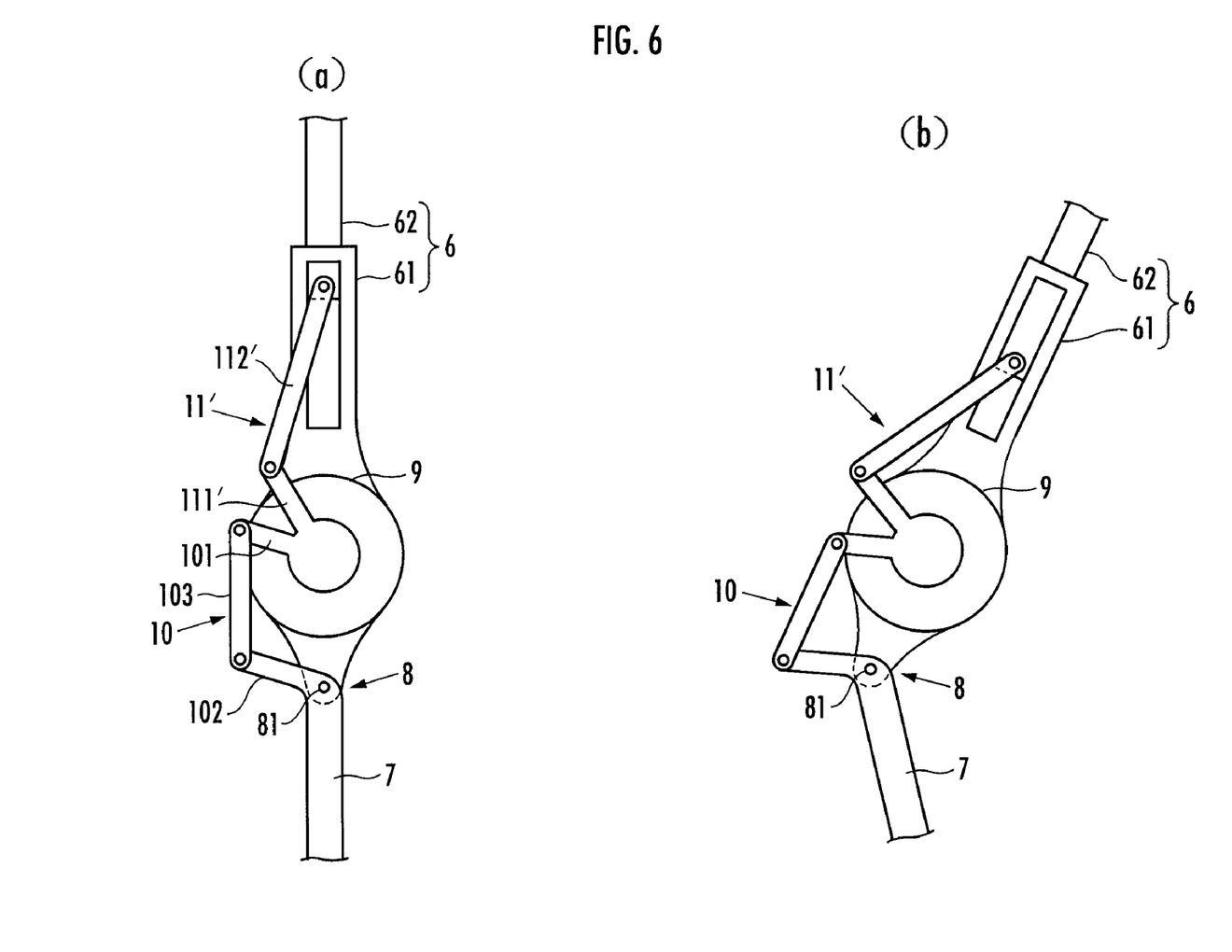
FIG. 6(a) is a side view of a leg link according to a second embodiment when it is extended.
FIG. 6(b) is a side view of the leg link when it is bent.

Although the second link 7 has been formed by the extensible and retractable link in the first embodiment, it is also possible to form the first link 6 by an extensible and retractable link, which can be freely extended and retracted, including a lower half portion 61 connected to the third joint portion 8 and an upper half portion 62 supported slidably by the lower half portion 61 as described in the second embodiment shown in FIG. 6. In this regard, in the second embodiment, the third joint portion 8 is driven via the power transmission system 10 by means of the driving source 9 mounted on the lower half portion 61 of the first link 6. Similarly to the first embodiment, the power transmission mechanism 10 includes a first crank arm 101 provided on the output side of the driving source 9, a second crank arm 102 extending beyond the joint shaft 81 with being integrated with the second link 7, and a rod 103 which connects the crank arms 101 and 102 to each other. An interlock system 11' is then provided which is formed by a mechanical system which converts the rotary motion of the driving source 9 to a linear motion for extending and retracting the first link 6, in other words, to a linear motion of the upper half portion 62 of the first link 6, so that the first link 6 is retracted and extended in conjunction with the operation of increasing and decreasing the flexion angle of the third joint portion 8.

The interlock system 11' includes a crank arm 111' provided on the output side of the driving source 9 and a connecting link 112' which connects the crank arm 111' to the upper half portion 62 of the first link 6. If the flexion angle of the third joint portion 8 increases, the upper half portion 62 of the first link 6 moves downward with respect to the lower half portion 61 and the first link 6 is retracted as shown in FIG. 6(b). If the flexion angle of the third joint portion 8 decreases, the upper half portion 62 of the first link 6 moves upward with respect to the lower half portion 61 and the first link 6 is extended as shown in FIG. 6(a). Thereby, the same working and effect as the first embodiment can be achieved.

In addition, it is also possible to combine the first embodiment with the second embodiment by forming both of the first link 6 and the second link 7 using extensible and retractable links, respectively, so that the first and second links 6 and 7 are retracted and extended in conjunction with the operation of increasing and decreasing the flexion angle of the third joint portion 8.

Although the embodiments of the present invention have been described hereinabove with reference to the drawings, the present invention is not limited thereto. For example, while the first joint portion 3 includes an arc-shaped guide rail 31 and the forward/backward swing fulcrum 3a of each leg link 5 in the first joint portion 3 is located above the seat member 1 in this embodiment, the first joint portion 3 can be formed by a simple-structured joint portion having a lateral shaft pivotally supporting the upper end portion of each leg link 5 so as to be free to swing in the anteroposterior direction. Furthermore, the load transfer portion can be formed by a harness to be attached around the user's waist. Moreover, to assist a user who is handicapped in one leg due to a fracture or the like of the leg in walking, it is possible to leave only the leg link on the side of the user's handicapped leg of the left and right leg links 5, 5 in the above embodiment, while omitting the other leg link.

What is claimed is:

1. A walking assisting device having a load transfer portion, a foot attachment portion attached to a user's foot, and a leg link between the load transfer portion and the foot attachment portion, in which a force generated by the leg link is transmitted to a user's trunk via the load transfer portion,
   wherein the leg link includes an upper first link connected to the load transfer portion via a first joint portion, a lower second link connected to a foot attachment portion via a second joint portion, a middle third joint portion which connects the first link to the second link so as to be free to bend and stretch, and a driving source which drives the third joint portion; and
   wherein at least one of the first link and the second link is formed by an extensible and retractable link, which can be freely extended and retracted, and an interlock system is provided which retracts and extends the extensible and retractable link in conjunction with an operation of increasing and decreasing a flexion angle of the third joint portion.

2. The walking assisting device according to claim 1, wherein the interlock system is adapted so that an extension speed of the extensible and retractable link, which is obtained by differentiating a length of the extensible and retractable link with respect to the flexion angle of the third joint portion, does not become zero even if the flexion angle of the third joint portion is brought to zero degree.

3. The walking assisting device according to claim 1, wherein the interlock system is formed by a mechanical system which converts a rotary motion of the third joint portion to a linear motion for extending and retracting the extensible and retractable link.

4. The walking assisting device according to claim 2, wherein the interlock system is formed by a mechanical system which converts a rotary motion of the third joint portion to a linear motion for extending and retracting the extensible and retractable link.

5. The walking assisting device according to claim 1, wherein the interlock system is formed by a mechanical system which converts a rotary motion of the driving source to a linear motion for extending and retracting the extensible and retractable link.

6. The walking assisting device according to claim 2, wherein the interlock system is formed by a mechanical system which converts a rotary motion of the driving source to a linear motion for extending and retracting the extensible and retractable link.

* * * * *